United States Patent

Mendez Llatas et al.

[11] Patent Number: 6,018,064
[45] Date of Patent: Jan. 25, 2000

[54] METALLOCENE COMPOUNDS, SYNTHESIS PROCESS AND USE THEREOF

[75] Inventors: Luis Mendez Llatas, Mostoles; Antonio Muñoz-Escalona Lafuente, Madrid, both of Spain

[73] Assignee: Repsol Quimica S.A., Madrid, Spain

[21] Appl. No.: 09/016,210

[22] Filed: Jan. 30, 1998

[30] Foreign Application Priority Data

Feb. 1, 1997 [ES] Spain ..................................... 9700200

[51] Int. Cl.$^7$ .............................. C07F 17/00; C07F 7/00; C07F 9/00
[52] U.S. Cl. ................................ 556/11; 556/12; 556/21; 556/43; 556/53; 556/58; 502/103; 502/117; 526/160; 526/943; 534/15
[58] Field of Search .................................. 556/11, 12, 21, 556/58, 43, 53; 502/103, 117; 526/160, 943; 534/15

[56] References Cited

U.S. PATENT DOCUMENTS 5,753,769  5/1998  Ueda et al. ............................. 525/323

*Primary Examiner*—Porfirio Nazario-Gonzalez
*Attorney, Agent, or Firm*—Ladas & Parry

[57] ABSTRACT

It is shown metallocences with functionalized bridge of formula

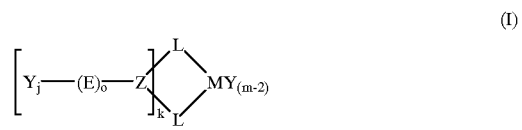

(I)

wherein M represents a transition metal from groups 3, 4, 5 or 6, L represents cyclopentadienyl-type ligands, Y represents a halogen and which can own one or various bridges between unities L. At least one of these bridges is functionalized through a group constituted by the union between a halogen atom and a silicon, germanium or tin atom. It is also shown a method for the synthesis of these metallocene compounds starting from the corresponding metallic halure and a precursor of the ligand with leaving groups. The functionalization shown by these compounds give them a peculiar reactivity that can be used for the formation of new metallocene derivatives, including bi- or poly-metallocene compounds. This reactivity is shown in the present document through examples with alcohol-type substrates.

21 Claims, No Drawings

METALLOCENE COMPOUNDS, SYNTHESIS PROCESS AND USE THEREOF

STATE OF THE ART PRIOR TO THE INVENTION

The metallocene compounds field has experimented a big development since the first syntheses of these compounds in the fifties (G. Wilkinson et al., *J. Am. Chem. Soc.*, 1953, 75, 1011). This development is basically due to the large increase in the number of applications wherein these compounds are used. So, they can be used as catalysts of hydrogenation, epoxidation, double bond isomerization, ketons reduction, aldolic reaction, synthesis of different substituted olefins, etc., but their largest use is as catalyst components for olefin polymerization, as they can be activated for this use by alumoxanes or other non-coordinative anion precursors (for example boron compounds). In this field metallocenes of group 4 (Ti, Zr, Hf) in particular have been developed, but also metallocenes of group 3, 5 and 6. Metallocenes were prepared for working in very different conditions (solution, suspension, mass, gas phase, high pressure and temperature processes, etc.). They were used for polymerizing and copolymerizing simple a-olefins, basically ethylene and propylene, but also more complex olefins (cyclolefins, diolefins and also olefins with polar groups; for example W. A. Nugent et al., *J. Am. Chem. Soc.* 1989, 111, 6435; R. M. Waymouth et al., *J. Am. Chem. soc.* 1992, 114, 9679; H Yasuda et al., *Macromol. Chem Phys*, 1995, 196, 2417).

For adapting to the different needs of each application very different metallocenes were synthesized, basically differing for the different substitution around the cyclopentadienyl rings that form it, as it is possible to influence in this way, both sterically and electronically, the reactivity of their active centers. An especially relevant development was the introduction of at least one bridge connecting the two cyclopentadienyl rings (H. H. Britzinger et al., *J. Organomet. Chem.*, 1979, 173, 6270), as it influenced the reactivity of the metallocene not only for its own steric and electronic nature, but also for (1) influencing the monomer greater or smaller accessibility to the active center as the bridge largerly determines the angle spread between the cyclopentadienyl rings and (2) for preventing the free rotation of the rings and, therefore, determining the symmetry of the whole molecule. With this it has been obtained a better stability of certain metallocenes, a greater or smaller discrimination of the monomers that are incorporated into the polymer because of their size and the possibility of obtaining or not stereoregolar polymers starting from a-olefins (isotactic, syndiotactic, hemiisotactic).

EP-A-757053 discloses new metallocenes characterized by the following general formula: $X_mM(L—M^2(R^1R^2)—A—ZR^3_oHal_p)_n$, wherein M is a metal of group 4, 5 or 6 of the periodic table, each X is independently selected from hydrogen, halogen or a $C_1$–$C_{40}$ carbon-containing rest; m is equal to 1, 2 or 3; n is equal to 1 or 2; each L is independently a π ligand, which coordinates to the central atom M; each $M^2$ is independently selected from silicon, germanium or tin; $R^1$ is a $C_1$–$C_{20}$ carbon-containing group; $R^2$ is a $C_1$–$C_{20}$ carbon-containing group or a π ligand, which coordinates to the central atom M; each A is independently a divalent $C_1$–$C_{40}$ carbon-containing rest; each Z is independently selected from boron, silicon, germanium or tin; each $R^3$ is independently selected from hydrogen or a $C_1$–$C_{20}$ carbon-containing rest; o is equal to 0, 1 or 2; each Hal is independently selected from a halogen atom; p is equal to 1, 2 or 3.

The compounds are characterized by the presence of the hydrocarbon bridge connecting two silicon, germanium or tin atoms to whom the halogen atom is connected. This characteristic makes them especially suitable in the preparation of supported catalysts. There is no mention of their possible use in the preparation of further functionalized metallocenes.

The invention object of the present application introduces a clear advantage as it develops even more the influence of the bridge in the metallocene structure, for providing this bridge with a functionality, that is to say a unity able to react with determined substrates. The object of the introduction of this functionality is the possibility of modifying the metallocenes through that reactive center. This can allow, among other applications, a new simple method for obtaining new di- or polymetallocene compounds, these compounds being those which show more than one metallocene unit in their structure. As it can result evident for a person skilled in this field, the fact of localizing the functionality in the bridge instead of other parts of the molecule has the advantage of maintaining this reactive position away from the catalytically active metallocene center.

DESCRIPTION OF THE INVENTION

In this invention it is described organometallic compounds of transition metals of groups of 3, 4, 5 or 6 of the periodic table of metallocene-type. Besides, the compounds of the present invention are characterized in that they have at least one union or bridge between the cyclopentadienyl type unites. The bridge is characterized in that it shows at least one functionality, this being a Si—Y, Ge—Y or Sn-Y-type unity, preferably Si—Y, Y being halogen.

In the present invention it is also described a synthesis method of these compounds, characterized by the use of leaving groups on cyclopentadienyl unities so that, through the reaction with the corresponding transition metal halide, a π union is realized between the metal and the cyclopentadienyl unity characteristic of the metallocenes. Besides, in the present invention it is described the use of these compounds in the synthesis of bi- or polymetallocene compounds. The invention refers in general to metallocenes represented by the following formula (Formula I)

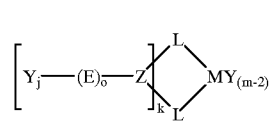

(I)

Wherein:

Y is halogen;

M is a transition metal of groups 3–6 of the periodic table;

each L is selected from a cyclopentadienyl-type unity, including indenyl or fluorenyl, substituted or not and the substituents being equal or different, unit to M through a π bond; Z is a group that forms a union bridge between the two unities L, which can have between 0 and 20 carbon atoms and between 0 and 5 oxygen, sulfur, nitrogen, phosphorus, silicon, germanium, tin or boron atoms;

E is a spacer group that unites Z and Y and can have between 0 and 20 carbon atoms and between 0 and 5 oxygen, sulfur, nitrogen, phosphorus, silicon, germanium, tin or boron atoms. It is characterized for having in its skeleton at least one silicon, germanium or tin atom, which the substituent Y is unit to;

o is a number of value 0 or 1;

k is a number of value 1, 2 or 3;

m is a number equal to or higher than 2 and coinciding with the oxidation state of the transition metal;

j is a number of value 0 or 1 with the condition that its value is 1 at least once; when j is equal to 1 and o is equal to O, Z is characterized by having at least one silicon, germanium or tin atom which Y is directly united to; with the proviso that the compound does not have general formula $$X_{m'}.M^1(L'\text{—}M^2)R^1R^2)\text{—}A'\text{—}Z'R^3{}_o.Hal_{p'})_{n'},$$

wherein $M^1$ is a metal of group 4, 5 or 6 of the periodic table, each X is independently selected from hydrogen, halogen or a $C_1$–$C_{40}$ carbon-containing rest; m' is equal to 1, 2 and 3; n' is equal to 1 or 2; each L' is independently a π ligand, which coordinates to the central atom $M^1$; each $M^2$ is independently selected from silicon, germanium or tin; $R^1$ is a $C_1$–$C_{20}$ carbon-containing group; $R^2$ is a $C_1$–$C_{20}$ carbon-containing group or a π ligand, which coordinates to the central atom $M^1$; each A' is independently a divalent $C_1$–$C_{40}$ carbon-containing rest; each Z' is independently selected from boron, silicon, germanium or tin; each $R^3$ is independently selected from hydrogen or a $C_1$–$C_{20}$ carbon-containing rest; o' is equal to 0, 1 or 2; each Hal is independently selected from a halogen atom; p' is equal to 1, 2 or 3.

The invention preferably refers to metallocenes represented by the following formula (formula II):

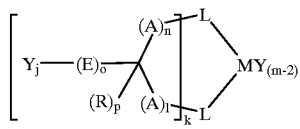

(II)

wherein:

Y is halogen;

M is a transition metal of groups 3, 4, 5 or 6 of the periodic table; each L is selected from a cyclopentadienyl-type unity, including idenyl or fluorenyl, substituted or not and the substituents being equal or different, united to M through a π bond;

Q is an element of group 13, 14 or 15;

E is a spacer group that unites Q and Y and can have between 0 and 20 carbon atoms and between 0 and 5 oxygen, sulfur, nitrogen, phosphorus, silicon, germanium, tin or boron atoms and it is characterized by having in its skeleton at least one silicon, germanium or tin atom, which the substituent Y is united to;

R is an atom of hydrogen, halogen, halocarbon, substituted halocarbon, $C_1$–$C_{20}$alkyl, $C_2$–$C_{20}$alkenyl, $C_6$–$C_{20}$aryl, $C_7$–$C_{40}$alkylaryl, $C_7$–$C_{40}$arylalkyl, $C_8$–$C_{20}$arylalkenyl, alkoxy, siloxy and combinations thereof;

A, equal to or different from each other, is a bridge group between unities L and Q constituted either by only one divalent atom of group 16, preferably —O—, or by a trivalent monosubstituted element of group 15, preferably >N—R, R being defined above, or a tetravalent disubstituted element of group 14, preferably >C(R)$_2$ or >Si(R)$_2$, R being defined above, or by a chain of 2 or more atoms substituted or not, this chain being preferably of type —C—C—, —C—Si—, —Si—Si—, —Si—O—, —C—O, —C—N—, —C—C—C, —C—Si—C—, —Si—O—Si—;

o is a number of value 0 or 1 with the condition that when it is equal to 0, Q is a silicon, germanium or tin atom;

k is a number of value 1, 2 or 3;

m is a number equal to or higher than 2 and coinciding with the oxidation state of the transition metal;

p, n, l are numbers of value 0 or 1;

j is a number of value 0 or 1 with the condition that its value is 1 at least once; when j is equal to 1 and o is equal to 0, Q is a silicon, germanium or tin atom; with the proviso that the compound does not have general formula $$X_{m'}.M^1(L'\text{—}M^2)(R^1R^2)\text{—}A'\text{—}Z'R^3{}_o.Hal_{p'})_{n'},$$

wherein $M^1$ is a metal of group 4, 5 or 6 of the periodic table, each X is independently selected from hydrogen, halogen or a $C_1$–$C_{40}$carbon-containing rest; m' is equal to 1, 2 or 3; n' is equal to 1 or 2; each L' is independently a π ligand, which coordinates to the central atom $M^1$; each $M^2$ is independently selected from silicon, germanium or tin; $R^1$ is a $C_1$–$C_{20}$carbon-containing group; $R^2$ is a $C_1$–$C_{20}$carbon-containing group or a π ligand, which coordinates to the central atom $M^1$; each A' is independently a divalent $C_1$–$C_{40}$carbon-containing rest; each Z' is independently selected from boron, silicon, germanium or tin; each $R^3$ is independently selected from hydrogen or a $C_1$–$C_{20}$ carbon-containing rest; o' is equal to 0, 1 or 2; each Hal is independently selected from a halogen atom; p' is equal to 1, 2 or 3.

What follows are descriptive and non-limiting examples of the structural formulas of some metallocene compounds according to the present invention;

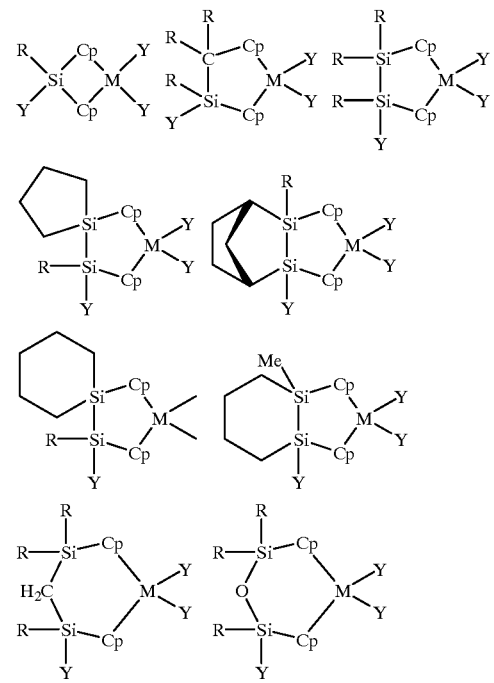

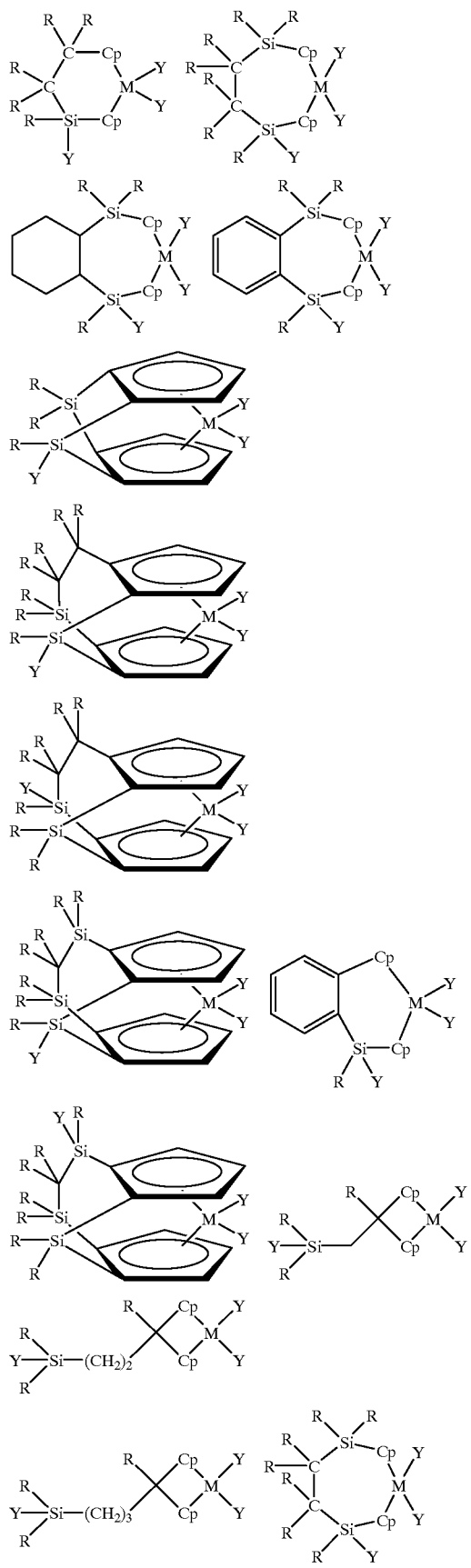
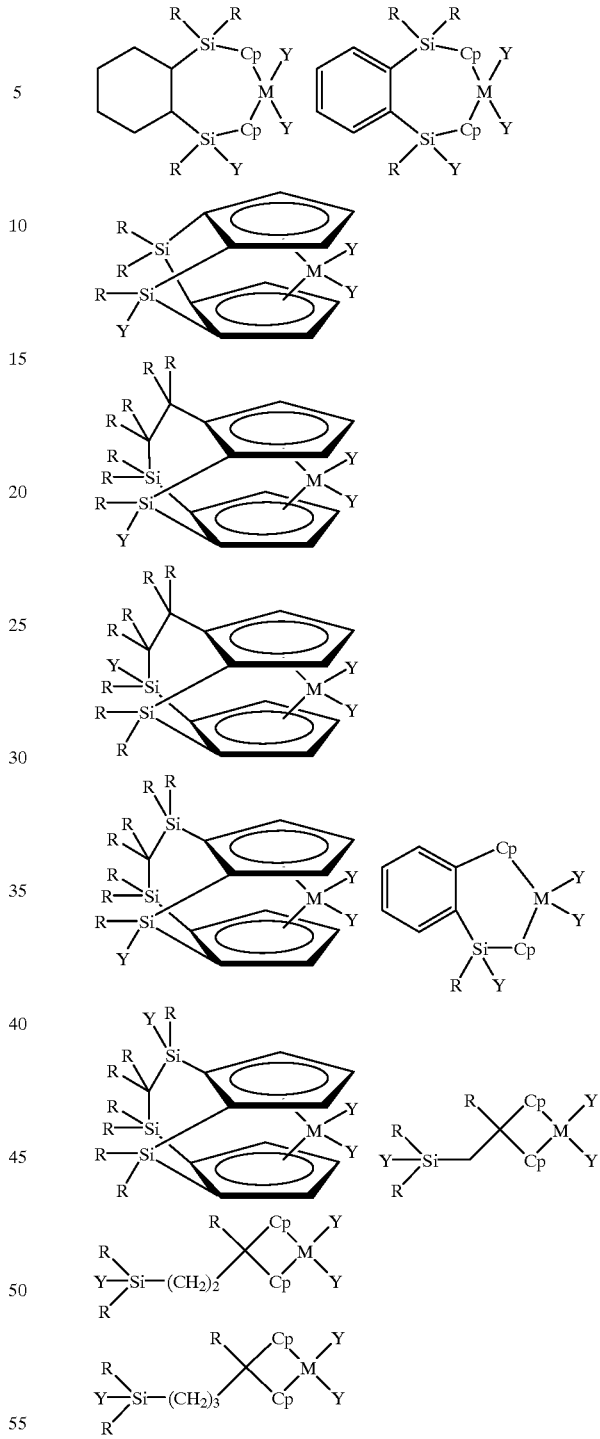

In these formulas the following symbols have been used:
Y, R and M; above defined
Cp: cyclopentadienyl or substituted cyclopentadienyl ring, also including in this definition substituted or not indenyl rings and substituted or not fluorenyl rings, Cp being able to represent in the same formula equal or different rings.
C, H, Si, O: atoms of the corresponding element of the periodic table.

What follows are descriptive and non-limiting examples of some metallocene compounds according to the present invention:

methyl-chloro-silanediyl-bis(cyclopentadienyl) zirconiumdichloride
methyl-chloro-silanediyl(cyclopentadienyl) (tetramethylcyclopentadienyl) zirconiumdichloride
methyl-chloro-silanediyl(cyclopentadienyl)1-indenyl) zirconiumdichloride
methyl-chloro-silanediyl(cyclopentadienyl)(1-(2-methy) indenyl) zirconiumdichloride
methyl-chloro-silanediyl(cyclopentadienyl)(9-fluorenyl) zirconiumdichloride
methyl-chloro-silanediyl bis(cyclopentadienyl) zirconiumdichloride
methyl-chloro-silanediyl(tetramethylcyclopentadienyl)(1-(2-methy)indenyl) zirconiumdichloride
methyl-chloro-silanediyl(tetramethylcyclopentadienyl)(1-indenyl) zirconiumdichloride
methyl-chloro-silanediyl(tetramethylcyclopentadienyl)(9-fluorenyl) zirconiumdichloride
methyl-chloro-silanediyl bis (1-(2-methy)indenyl) zirconiumdichloride
methyl-chloro-silanediyl(1-(2-methy)indenyl)(1-indenyl) zirconiumdichloride
methyl-chloro-silanediyl(1-(2-methy)indenyl)(9-fluorenyl) zirconiumdichloride
methyl-chloro-silanediyl bis(1-indenyl) zirconiumdichloride
methyl-chloro-silanediyl(9-fluorenyl)(1-indenyl) zirconiumdichloride
methyl-chloro-silanediyl bis(9-fluorenyl) zirconiumdichloride
methyl-chloro-silanediyl bis(cyclopentadienyl) hafniumdichloride
methyl-chloro-silanediyl(cyclopentadiunyl) tetramethylcyclopentadienyl) hafniumdichloride
methyl-chloro-silanediyl(cyclopentadienyl)(1-indenyl) hafniumdichloride
methyl-chloro-silanediyl(cyclopentadienyl)(1-(2-methy) indenyl) hafniumdichloride
methyl-chloro-silanediyl(cyclopentadienyl)(9-fluorenyl) hafniumdichloride
methyl-chloro-silanediyl bis(tetramethylcyclopentadienyl) hafniumdichloride
methyl-chloro-silanediyl bis(tetramethylcyclopentadienyl) (1-(2-methy)indenyl) hafniumdichloride
methyl-chloro-silanediyl bis(tetramethylcyclopentadienyl) (1-indenyl) hafniumdichloride
methyl-chloro-silanediyl bis(tetramethylcyclopentadienyl) (9-fluorenyl) hafniumdichloride
methyl-chloro-silanediyl bis (1-(2-methy)indenyl) hafniumdichloride
methyl-chloro-silanediyl(1-(2-methy)indenyl)(1-indenyl) hafniumdichloride
methyl-chloro-silanediyl(1-(2-methy)indenyl)(9-fluorenyl) hafniumdichloride
methyl-chloro-silanediyl bis(1-indenyl) hafniumdichloride
methyl-chloro-silanediyl(9-fluorenyl)(1-indenyl) hafniumdichloride
methyl-chloro-silanediyl(9-fluorenyl) hafniumdichloride
methyl-chloro-silanediyl-bis(cyclopentadienyl) titaniumdichloride
methyl-chloro-silanediyl(cyclopentadienyl) (tetramethylcyclopentadienyl) titaniumdichloride
methyl-chloro-silanediyl(cyclopentadienyl)(1-indenyl) titaniumdichloride
methyl-chloro-silanediyl(cyclopentadienyl)(1-(2-methy) indenyl) titaniumdichloride
methyl-chloro-silanediyl(cyclopentadienyl)(9-fluorenyl) titaniumdichloride
methyl-chloro-silanediyl bis(cyclopentadienyl) titaniumdichloride
methyl-chloro-silanediyl(tetramethylcyclopentadienyl)(1-(2-methy)indenyl) titaniumdichloride
methyl-chloro-silanediyl(tetramethylcyclopentadienyl)(1-indenyl) titaniumdichloride
methyl-chloro-silanediyl(tetramethylcyclopentadienyl)(9-fluorenyl) titaniumdichloride
methyl-chloro-silanediyl bis (1-(2-methy)indenyl) titaniumdichloride
methyl-chloro-silanediyl(1-(2-methy)indenyl)(1-indenyl) titaniumdichloride
methyl-chloro-silanediyl(1-(2-methy)indenyl)(9-fluorenyl) titaniumdichloride
methyl-chloro-silanediyl bis(1-indenyl) titaniumdichloride
methyl-chloro-silanediyl(9-fluorenyl)(1-indenyl) titaniumdichloride
methyl-chloro-silanediyl bis(9-fluorenyl) titaniumdichloride
ethyl-chloro-silanediyl bis(cyclopentadienyl) zirconiumdichloride
ethyl-chloro-silanediyl(cyclopentadiunyl) tetramethylcyclopentadienyl) zirconiumdichloride
ethyl-chloro-silanediyl(cyclopentadienyl)(1-indenyl) zirconiumdichloride
ethyl-chloro-silanediyl(cyclopentadienyl)(1-(2-methy) indenyl) zirconiumdichloride
ethyl-chloro-silanediyl(cyclopentadienyl)(9-fluorenyl) zirconiumdichloride
ethyl-chloro-silanediyl bis(tetramethylcyclopentadienyl) zirconiumdichloride
ethyl-chloro-silanediyl(tetramethylcyclopentadienyl)(1-(2-methy)indenyl) zirconiumdichloride
ethyl-chloro-silanediyl(tetramethylcyclopentadienyl)(1-indenyl) zirconiumdichloride
ethyl-chloro-silanediyl(tetramethylcyclopentadienyl)(9-fluorenyl) zirconiumdichloride
ethyl-chloro-silanediyl bis (1-(2-methy)indenyl) zirconiumdichloride
ethyl-chloro-silanediyl(1-(2-methy)indenyl)(1-indenyl) zirconiumdichloride
ethyl-chloro-silanediyl(1-(2-methy)indenyl)(9-fluorenyl) zirconiumdichloride
ethyl-chloro-silanediyl bis(1-indenyl) zirconiumdichloride
ethyl-chloro-silanediyl(9-fluorenyl)(1-indenyl) zirconiumdichloride
ethyl-chloro-silanediyl bis(9-fluorenyl) zirconiumdichloride
ethyl-chloro-silanediyl-bis(cyclopentadienyl) hafniumdichloride
ethyl-chloro-silanediyl(cyclopentadienyl) (tetramethylcyclopentadienyl) hafniumdichloride
ethyl-chloro-silanediyl(cyclopentadienyl)(1-indenyl) hafniumdichloride
ethyl-chloro-silanediyl(cyclopentadienyl)(1-(2-methy) indenyl) hafniumdichloride
ethyl-chloro-silanediyl(cyclopentadienyl)(9-fluorenyl) hafniumdichloride
ethyl-chloro-silanediyl bis(cyclopentadienyl) hafniumdichloride
ethyl-chloro-silanediyl(tetramethylcyclopentadienyl)(1-(2-methy)indenyl) hafniumdichloride
ethyl-chloro-silanediyl(tetramethylcyclopentadienyl)(1-indenyl) hafniumdichloride
ethyl-chloro-silanediyl(tetramethylcyclopentadienyl)(9-fluorenyl) hafniumdichloride ethyl-chloro-silanediyl bis (1-(2-methy)indenyl) hafniumdichloride
ethyl-chloro-silanediyl(1-(2-methy)indenyl)(1-indenyl) hafniumdichloride
ethyl-chloro-silanediyl(1-(2-methy)indenyl)(9-fluorenyl) hafniumdichloride
ethyl-chloro-silanediyl bis(1-indenyl) hafniumdichloride
ethyl-chloro-silanediyl(9-fluorenyl)(1-indenyl) hafniumdichloride
ethyl-chloro-silanediyl bis(9-fluorenyl) hafniumdichloride
ethyl-chloro-silanediyl bis(cyclopentadienyl) titaniumdichloride
ethyl-chloro-silanediyl(cyclopentadiunyl) tetramethylcyclopentadienyl) titaniumdichloride
ethyl-chloro-silanediyl(cyclopentadienyl)(1-indenyl) titaniumdichloride
ethyl-chloro-silanediyl(cyclopentadienyl)(1-(2-methy)indenyl) titaniumdichloride
ethyl-chloro-silanediyl(cyclopentadienyl)(9-fluorenyl) titaniumdichloride
ethyl-chloro-silanediyl bis(tetramethylcyclopentadienyl) titaniumdichloride
ethyl-chloro-silanediyl(tetramethylcyclopentadienyl)(1-(2-methy)indenyl) titaniumdichloride
ethyl-chloro-silanediyl(tetramethylcyclopentadienyl)(1-indenyl) titaniumdichloride
ethyl-chloro-silanediyl(tetramethylcyclopentadienyl)(9-fluorenyl) titaniumdichloride
ethyl-chloro-silanediyl bis (1-(2-methy)indenyl) titaniumdichloride
ethyl-chloro-silanediyl(1-(2-methy)indenyl)(1-indenyl) titaniumdichloride
ethyl-chloro-silanediyl(1-(2-methy)indenyl)(9-fluorenyl) titaniumdichloride
ethyl-chloro-silanediyl bis(1-indenyl) titaniumdichloride
ethyl-chloro-silanediyl(9-fluorenyl)(1-indenyl) titaniumdichloride
ethyl-chloro-silanediyl bis(9-fluorenyl) titaniumdichloride
propyl-chloro-silanediyl-bis(cyclopentadienyl) zirconiumdichloride
propyl-chloro-silanediyl(cyclopentadienyl) (tetramethylcyclopentadienyl) zirconiumdichloride
propyl-chloro-silanediyl(cyclopentadienyl)(1-indenyl) zirconiumdichloride
propyl-chloro-silanediyl(cyclopentadienyl)(1-(2-methy)indenyl) zirconiumdichloride
propyl-chloro-silanediyl(cyclopentadienyl)(9-fluorenyl) zirconiumdichloride
propyl-chloro-silanediyl bis(cyclopentadienyl) zirconiumdichloride
propyl-chloro-silanediyl(tetramethylcyclopentadienyl)(1-(2-methy)indenyl) zirconiumdichloride
propyl-chloro-silanediyl(tetramethylcyclopentadienyl)(1-indenyl) zirconiumdichloride
propyl-chloro-silanediyl(tetramethylcyclopentadienyl)(9-fluorenyl) zirconiumdichloride
propyl-chloro-silanediyl bis (1-(2-methy)indenyl) zirconiumdichloride
propyl-chloro-silanediyl(1-(2-methy)indenyl)(1-indenyl) zirconiumdichloride
propyl-chloro-silanediyl(1-(2-methy)indenyl)(9-fluorenyl) zirconiumdichloride
propyl-chloro-silanediyl bis(1-indenyl) zirconiumdichloride
propyl-chloro-silanediyl(9-fluorenyl)(1-indenyl) zirconiumdichloride
propyl-chloro-silanediyl bis(9-fluorenyl) zirconiumdichloride
propyl-chloro-silanediyl bis(cyclopentadienyl) hafniumdichloride
propyl-chloro-silanediyl(cyclopentadiunyl) tetramethylcyclopentadienyl) hafniumdichloride
propyl-chloro-silanediyl(cyclopentadienyl)(1-indenyl) hafniumdichloride
propyl-chloro-silanediyl(cyclopentadienyl)(1-(2-methy)indenyl) hafniumdichloride
propyl-chloro-silanediyl(cyclopentadienyl)(9-fluorenyl) hafniumdichloride
propyl-chloro-silanediyl bis(tetramethylcyclopentadienyl) hafniumdichloride
propyl-chloro-silanediyl(tetramethylcyclopentadienyl)(1-(2-methy)indenyl) hafniumdichloride
propyl-chloro-silanediyl(tetramethylcyclopentadienyl)(1-indenyl) hafniumdichloride
propyl-chloro-silanediyl(tetramethylcyclopentadienyl)(9-fluorenyl) hafniumdichloride
propyl-chloro-silanediyl bis (1-(2-methy)indenyl) hafniumdichloride
propyl-chloro-silanediyl(1-(2-methy)indenyl)(1-indenyl) hafniumdichloride
propyl-chloro-silanediyl(1-(2-methy)indenyl)(9-fluorenyl) hafniumdichloride
propyl-chloro-silanediyl bis(1-indenyl) hafniumdichloride
propyl-chloro-silanediyl(9-fluorenyl)(1-indenyl) hafniumdichloride
propyl-chloro-silanediyl bis(9-fluorenyl) hafniumdichloride
propyl-chloro-silanediyl-bis(cyclopentadienyl) titaniumdichloride
propyl-chloro-silanediyl(cyclopentadienyl) (tetramethylcyclopentadienyl) titaniumdichloride
propyl-chloro-silanediyl(cyclopentadienyl)(1-indenyl) titaniumdichloride
propyl-chloro-silanediyl(cyclopentadienyl)(1-(2-methy)indenyl) titaniumdichloride
propyl-chloro-silanediyl(cyclopentadienyl)(9-fluorenyl) titaniumdichloride
propyl-chloro-silanediyl bis(cyclopentadienyl) titaniumdichloride
propyl-chloro-silanediyl(tetramethylcyclopentadienyl)(1-(2-methy)indenyl) titaniumdichloride
propyl-chloro-silanediyl(tetramethylcyclopentadienyl)(1-indenyl) titaniumdichloride
propyl-chloro-silanediyl(tetramethylcyclopentadienyl)(9-fluorenyl) titaniumdichloride
propyl-chloro-silanediyl bis (1-(2-methy)indenyl) titaniumdichloride
propyl-chloro-silanediyl(1-(2-methy)indenyl)(1-indenyl) titaniumdichloride
propyl-chloro-silanediyl(1-(2-methy)indenyl)(9-fluorenyl) titaniumdichloride
propyl-chloro-silanediyl bis(1-indenyl) titaniumdichloride
propyl-chloro-silanediyl(9-fluorenyl)(1-indenyl) titaniumdichloride
propyl-chloro-silanediyl bis(9-fluorenyl) titaniumdichloride The synthesis of the functionalized metallocenes object of the present invention can be obtained according to the general method represented in the following scheme.

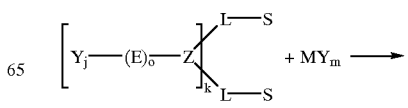

-continued

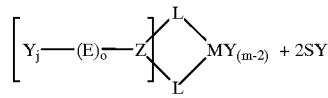

being:
- X, Z, L, E, M, j, m and o defined above;
- S: leaving group united to the cyclopentadienyl ring, preferably constituted by a unity $T(R^4)_3$, T being silicon, germanium or tin and $R^4$ is $C_1$–$C_{20}$alkyl.
- S represents preferably groups $Si(CH_3)_3$ and $Sn(CH_3)_3$. In case represented by this scheme, S can represent unities equal to or different from each other; the union L—S can represent an ionic, s, or p bond or combinations thereof; the union L—M always represents a bond with a high π character. This process for the synthesis of metallocenes with functionalized bridge can be realized in the presence of solvent or not. In case a solvent is used, this can be preferably an aliphatic hydrocarbon, an aromatic hydrocarbon, or mono or polyhalogen containing derivatives therefrom. A mixture of two or more solvents can be used too.

This synthesis process of metallocenes with functionalized bridge can be realized in a temperature range between −20 and 300° C., preferably between 0 and 200° C., or at the reflux temperature of the used solvents system.

This process for the synthesis of metallocenes with functionalized bridge can be realized with or without protection from light.

The compounds object of the present invention can be on their turn used as precursors of new compounds or materials, obtained by the action of a fit substrate on the functionalization of the starting compounds. A fit substrate is one that has at least one reactive group of type G—J, G representing an element of groups 14, 15, 16 or 17 and J representing an element of groups 1 (including hydrogen), 2 or 3.

The reaction process between both reactive groups, that is to say the metallocene functional group and the substrate reactive group, can be represented by the following equation

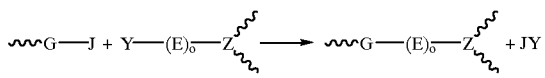

wherein
the symbol

∼∼∼ is used in this context to represent the union of said reactive groups with the rest of the compound wherein they are integrated;
G, J, Y, E, Z and o are defined above.

In this way metallocene derivatives can be obtained starting from functionalizated precursor metallocenes characterized by having one or various unities G—(E)$_o$—Z.

Reactive groups G—J are, for example; hydroxy, amine, phosphino, thiol, hydroxy, amido, phosphido, thioxy, alkyl anions etc. Examples of substrates containing these groups are: water, ammonia, silica, alumina, alcohols, phenols, silanols, thiols, primary and secondary amines, primary and secondary phosphines, hydrogen halides, alkylides or alcoxides or amidos or phenoxides or alcoxides or hydroxides of alkali or alcaliearth metals, or compounds that combine various unities among these, for example: aminoalchools, hydroxythiols, polyols, diols.

The reaction between the metallocene with a functionalized bridge and the substrate can be realized in a large range of conditions fundamentally depending on the nature of both reactants:

- Temperature—It can be in a large range from −100 to 200° C., preferably between −20 to 180° C., the higher and lower limits being fundamentally conditioned by the activity, solubility and stability of the reactants.
- Solvent—In general, it can be said that this type of reaction can be realized in a large variety of solvents, for example: aliphatic and aromatic hydrocarbons, but it is preferable to use coordinating solvents without acid hydrogens. Solvents of this type are ethers, thioethers, tertiary amines, nitrils, secondary amides etc. Non-coordinating solvents can be used as well, which a coordinating agent is added to (ethers, thioethers, tertiary amines, nitrils, secondary amides etc) in order to aid the reaction.
- Reaction time—The necessary time for a complete reaction mostly depends on the variables cited before (temperature and solvent) as well as on the activity of the reactants themselves. In general it can be said that it can range between various minutes and various days.

As a consequence of the fact that the same substrate can present various reactive groups of different nature and as it can be evident for a person skilled in the art, the possible compounds and materials obtained starting from the metallocences functionalized according to the present invention are practically unlimited. A particularly interesting case can be the obtaining of bimetallocene or polymetallocene derivatives obtained starting from the reaction between a substrate with two or more groups G—J and various metallocenes with different functionalized bridges. What follows are some examples of the derivatives of the metallocenes functionalized in the bridge, as a clarification which does not imply any restriction.

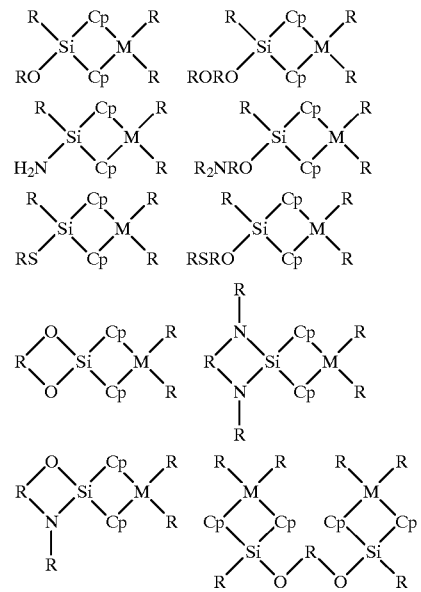

-continued

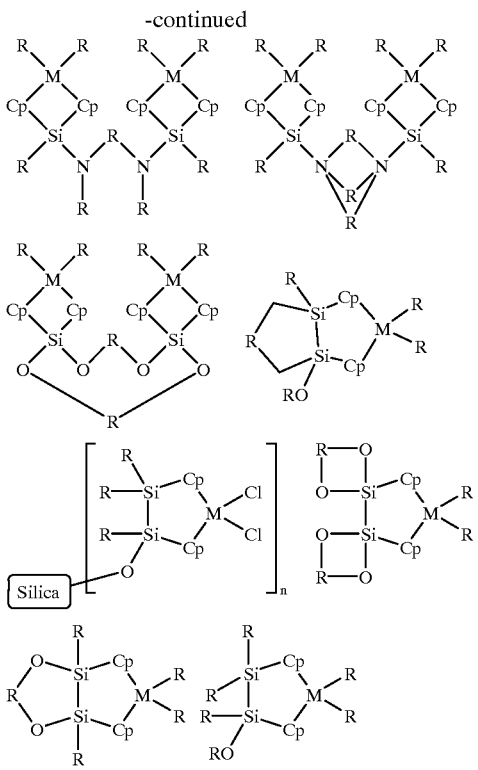

In these pictures R, M, Cp have the above defined meaning. Si, O, N, S symbolize an atom of the corresponding element according to the periodic table.

Both the functionalized metallocenes object of the present invention and their derivatives, including those supported on inorganic solids, can be used in various functions, their use as catalyst components for α-olefins polymerization reactions in conjunction with one or various cocatalysts being a special case.

EXAMPLES

General conditions: The metallocenes synthesis was realized in all its steps under the protection of an atmosphere of dry nitrogen, either in a dry box or by using the techniques Schlenk. The used solvents were dried before being used according to the methods described in literature. In the following examples these abbreviations are used for representing the written formulas:

Cp: cyclopentadienyl radical
Me: methyl radical
TMS: trimethylsilyl radical

Example 1
Synthesis of ((chloromethylsilandiyl)bis(cyclopentadienyl)) zirconium(IV)dichloride, Cl(Me)SiCp$_2$ZrCl$_2$ This example is useful for describing a zirconium metallocene with a functionalized bridge and its synthesis.

1.1 Preparation of the dilithium salt of cyclopentadienyltrimethylsilane, CpTMSLi A solution of 40 g (0.29 mol) of cyclopentadienyltrimethylsilane in 300 ml of hexane is added to 200 ml of a 1.25 M solution of butyllithium in hexane. During the addition of the reaction mixture the temperature is maintained at 0–5° C. After 3 h at room temperature, the obtained white solid is settled and washed once with 150 ml of hexane. This solid is identified as the desired product. $^1$H NMR (d$_8$-tetrahydrofurane) 5.95 (pseudo-t, 2H), 5.85 (pseudo-t, 2H), 0.16 (s, 9H). $^{13}$C-NMR (d$_8$-tetrahydrofurane) 112.9, 111.2, 108.09, 2.89.

1.2 Preparation of (dichloro(methyl)silyl(trimethylsilyl) cyclopentadiene, Cl$_2$(Me)SiCpTMS A solution of 30 ml (0.25 mol) of trichloromethylsilane and 250 ml of dry hexane is added to a suspension of 0.25 mol of CpTMSLi and 200 ml of hexane. Then, the reaction mixture is heated at the reflux temperature for 5 h. After cooling, the solid is filtered and washed with 200 more ml of hexane. From the union of the filtered product and the washing waters, after the elimination of the solvent in vacuum, a pale yellow oil that distils at 73–74° C. (2 Torr) is obtained. The obtained product is mostly the isomer 1-(dichloro(methyl)silyl)-1(trimethylsilyl)cyclopentadyene. Overall yield of steps 1.1 and 1.2: 66.7 g (92%). $^1$H-NMR (C$_6$D$_6$): 6.61 (m, 2H), 6.42 (m, 2H), 0.13 (s, 3H), 0.04 (s, 9H). $^{13}$C-NMR (C$_6$D$_6$): 134.2, 133.6, 59.0, 2.5, −1.1. 1.3 Preparation of bis(trimethylsilyleyclopentadienyl) methylchlorosilane, Cl(Me)Si(CpTMS), 80 ml of a 1M solution of [CpTMS]MgCl (chloromagnesium derivative of trimethylsilylcyclopentadienile) in tetrahydrofurane is slowly added to a solution of 20.2 g (0.08 mol) of [Cl$_2$(Me) SiCpTMS] prepared in 1.2 and 300 ml of hexane. The reaction mixture is maintained under stirring for 18 more h at room temperature. The solid is filtered and washed with hexane (100 ml ). The solvent of the filtered product is eliminated and the obtained oil is distilled. The pale yellow fraction that distils at 110° C. (0.5 Torr) is gathered. Yield 15.8 g (57%). This fraction consists in a mixture of isomers with formula Cl(Me)Si(CpTMS)$_2$.

1.4 Preparation of ((chloromethylsilanodiyl)bis (cyclopentadienyl))zirconium(IV)dichloride, Cl(Me)Si(Cp), ZrCl$_2$ A solution of 10.14 g (0.029 mol) of Cl(Me)Si(CpTMS)$_2$ and 200 of toluene is quickly transferred to 6.69 g (0.029 mol) of ZrCl$_4$ in a container protected from light. This is immediately introduced in a bath at 110° C. and maintained under stirring for 3 h. Then, it is filtered hot and the solution is immediately cooled in a freezer causing the crystallization of the product, which is gathered through filtration. Yield 7.7 g (72%). Zr 24.6% (theor.: 24.7%); Cl 28.1% (theor.: 28.8%). $^1$H-NMR (CDCl$_3$): 7.04 (m, 2H), 7.00 (m, 2H), 6.17 (m, 2H), 5.97 (m, 2H), 1.12 (s, 3H). $^{13}$C-NMR (CDCl$_3$); 129.5, 128.2, 114.5, 113.4, 108.2, −17. Mass spectrometry: M$^+$m/z (relative intensity) 373.9 (14%) 372.9 (8%), 371.9 (41%), 370.9 (18%), 369.9 (80%), 368.9 (36%), 367.9 (100%), 366.9 (30%), 365.9 (71%) [M$^+$calculated for C$_{11}$H$_{11}$Cl$_3$SiZr: 373.9 (13%), 372.9 (8%), 371.9 (41%), 370.9 (18%), 369.9 (77%), 368.9 (33%), 367.9 (100%), 366.9 (28%), 365.9 (73%)]

Example 2
Synthesis of ((chloromethylsilanodiyl)bis (cyclopentadienyl))hafnium(IV)dichloride, Cl(Me) SiCp$_2$HfCl$_2$.

This example describes a hafnium metallocene with functionalized bridge and its synthesis.

A solution of 2.15 g (6.1 mmol) of Cl(Me)Si(CpTMS)$_2$ and 50 ml of toluene is quickly added to 1.95 g (6.1 mmol) of HfCl$_4$ in a container protected from light. Then, it is soaked in an oil bath previously heated at 110° C. It is maintained under stirring under these conditions for 2 h, before filtering it hot. The so-obtained solution is cooled in a freezer. In this way, it is realized the crystallization of the desired product, which is identified as Cl(Me)SiCp$_2$HfCl$_2$. Yield: 2.1 g (78%). $^1$H-NMR (CDCl$_3$): 6.95 (m,2H), 6.10

(m, 2H), 5.90 (m,2H), 1.12 (s,3H). $^{13}$C-NMR (CDCl$_3$): 128.2, 126.9, 112.4, 109.5, −1.7. Masses spectrometry: M$^+$m/z (relative intensity) 460.9 (4%), 459.9 (19.5%), 458.9 (19%), 457.9 (65%), 456.9 (50%), 455.9 (100%), 454.9 (60%), 453.9 (55%), 452.9 (31%), 451.9 (10%) [M$^+$calculated for C$_{11}$H$_{11}$Cl$_3$SiHf: 460.9 (4%), 459.9 (21%), 458.9 (19%), 452.9 (70%), 456.9 (45%), 455.9 (100%), 454.9 (54%), 453.9 (51%), 452.9 (28%), 451.9 (8%)].

Example 3
Reaction of Cl(Me)SiCp$_2$HfCl$_2$ with H$_2$O

This example describes the process for obtaining a bimetallocene compound starting from metallocenes with functionalized bridge.

0.590 g (1.3 mmol) of the hafnocene prepared according to example 2 are dissolved in 40 ml of dry tetrahydrofurane under N$_2$. Then, 12 ml (0.66 mmol) of distilled water is added. It is maintained under stirring at room temperature for 12 h. Then, the solvent is eliminated in vacuum and the residue is extracted with diethyl ether. After the elimination of the solvent from the extracted phase, a solid, pale pink residue is left. Yield: 0.41 g (73%). It is identified as Cl$_2$HfCp$_2$Si(CH$_3$)—O—(CH$_3$)SiCp$_2$HfCl$_2$ {$^1$H-NMR (CDCl$_3$): 6.94 (m, 4H), 6.84 (m,4H), 6.07 (m,4H), 5.84 (m,4H), 0.86 (s,6H)}.

Example 4
Reaction of Cl(Me)SiCp$_2$ZrCl$_2$ with benzyl alcohol

This example describes the reaction between a metallocene with functionalized bridge and a monohydroxyl alcohol.

200 ml (1.9 mmol) of benzyl alcohol is added to a solution of 0.5 g (1.35 mmol) of Cl(Me)SiCp$_2$ZrCl$_2$ in 40 ml of dry tetrahydrofurane. It is maintained under stirring at room temperature for 12 h. Then, the solvent is evaporated in vacuum and diethyl either is added. The formed solid is gathered and it is identified as PhCH$_2$O(CH$_3$)SiCp$_2$ZrCl$_2$ {$^1$H-NMR (CDCl$_3$): 7.50-7.30 (m,5H), 7.03 (m,2H), 6.92 (m,2H), 6.10 (m,2H), 5.93 (m,2H), 5.15 (s,2H), 0.77 (s,3H). Masses spectrometry: M$^+$m/z (relative intensity) 446.0 (7%), 445.0 (6%), 444.0 (32%), 443.0 (19%), 442.0 (69%), 441.0 (39%), 440.0 (100%), 439.0 (45%), 438.0 (91%), [M$^+$calculated for C$_{18}$H$_{16}$Cl$_2$OSiZr: 446.0 (9%), 445.0 (8%), 444.0 (33%), 443.0 (20%), 442.0 (70%), 441.0 (38%), 440.0 (100%), 439.0 (44%), 438.0 (92%)].

Example 5
Reaction of Cl(Me)SiCp$_2$ZrCl$_2$ with 1,4-benzenedimethanol

This example describes the reaction between a metallocene with functionalized bridge and a diol.

A solution of 500 mg (1.35 mmol) of the zirconocene prepared in example 2 is added to a solution of 49 mg (0.35 mmol) of 1,4-benzenedimethanol in 30 ml of dry tetrahydrofurance. The reaction mixture is stirred at room temperature for more than 12 h. Then, the solvent is eliminated in vacuum and the residue is extracted with diethyl ether (50 ml). The solid residue consists of a mixture composed of:

67% Cl$_2$ZrCp$_2$Si(CH$_3$)—OCH$_2$C$_6$H$_4$CH$_2$O—(CH$_3$)SiCp$_2$ZrCl$_2$ {$^1$H-NMR (CDCl$_3$): 7.47 (s,4H), 7.03 (m), 6.92 (m), 6.08 (m), 5.93 (m), 5.16 (s,4H), 0.78 (s,6H)}

15% HOCH$_2$C$_6$H$_4$CH$_2$O—(CH$_3$)SiCp$_2$ZrCl$_2$ {$^1$H-NMR (CDCl$_3$): 7.42 (m,4H), 7.03 (m), 6.92 (m), 6.08 (m), 5.93 (m), 5.13 (s,2H), 4.74 (s,2H), 0.75 (s,3H)}

18% Cl$_2$ZrCp$_2$Si(CH$_3$)—O—(CH$_3$)SiCp$_2$ZrCl$_2$ {$^1$H-NMR (CDCl$_3$): 7.03 (m), 6.92 (m), 6.14 (m,4H), 5.93 (m), 0.84 (s,6H)}

We claim:

1. A metallocene compound having a formula I:

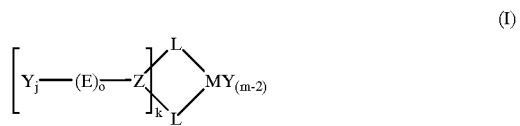

(I)

wherein:

Y is halogen

M is a transition metal of group 3, 4, 5 or 6 of the periodic table;

each L is independently selected from the group consisting of cyclopentadienyl-type groups, including indenyl and fluorenyl, wherein the cyclopentadienyl-type groups are optionally substituted with a substituent or substituents wherein the substituents are equal or different, wherein the L is united to M through a π bond;

Z is a group that forms a union bridge between the two L's, wherein Z can have between 0 and 20 carbon atoms and between 0 and 5 oxygen, sulphur, nitrogen, phosphorus, silicon, germanium, tin, or boron atoms;

E is a spacer group that unites Z and Y and can have between 0 and 20 carbon atoms and between 0 and 5 oxygen, sulphur, nitrogen, phosphorus, silicon, germanium, tin, or boron atoms, wherein the E has a skeleton with at least one silicon, germanium, or tin atom, and wherein the Y is united with the silicon, germanium, or tin atom of E;

o is a number of value 0 or 1;

k is a number of value 1, 2, or 3;

m is a number equal to or higher than 2 and coinciding with the oxidation state of the transition metal;

j is a number of value 0 or 1 ; when j is equal to 1 and o is equal to 0, z has at least one silicon, germanium or tin atom, wherein Y is directly united with the silicon, germanium, or tin atom of Z;

with a proviso that the compound does not have a general formula of:

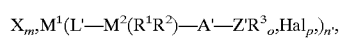

wherein M$^1$ is a metal of group 4, 5 or 6 of the periodic table, each X is independently selected from the group consisting of hydrogen, halogen, and a c$_1$–C$_{40}$ carbon-containing rest; m' is equal to 1, 2 or 3; n' is equal to 1 or 2; each L' is independently a π ligand, wherein L' coordinates to M$^1$; each M$^2$ is independently selected from the group consisting of silicon, germanium, and tin; R$^1$ is a C$_1$–C$_{20}$ carbon-containing group; R$^2$ is a C$_1$–C$_{20}$ carbon-containing group or a π ligand, wherein R$^2$ coordinates to M$^1$; each A' is independently a divalent C$_1$–C$_{40}$ carbon-containing rest; each z' is independently selected from the group consisting of boron, silicon, germanium, and tin; each R$^3$ is independently selected from the group consisting of hydrogen and a C$_1$–C$_{20}$ carbon-containing rest; o' is equal to 0, 1, or 2; each Hal is independently selected from the group consisting of halogen atoms; and p' is equal to 1, 2, or 3.

2. A metallocene compound according to claim 1, wherein the compound has a formula II:

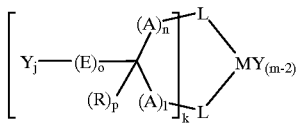

(II)

wherein:

Y is halogen;

M is a transition metal of group 3, 4, 5, or 6 of the periodic table;

each L is independently selected from the group consisting of cyclopentadienyl-type groups, including indenyl and fluorenyl, wherein the cyclopentadienyl-type groups are optionally substituted with a substituent or substituents wherein the substituents are equal or different, wherein the L is united to M through a $\pi$ bond;

Q is an element of group 13, 14, or 15;

E is a spacer group that unites Q and Y and can have between 0 and 20 carbon atoms and between 0 and 5 oxygen, sulphur, nitrogen, phosphorus, silicon, germanium, tin, or boron atoms, wherein the E has a skeleton with at least one silicon, germanium, or tin atom, and wherein the Y is united with the silicon, germanium, or tin atom of E;

R is selected from the group consisting of hydrogen, halogen, halocarbon, substituted halocarbon, $C_1$–$C_{20}$ alkyl, $C_2$–$C_{20}$ alkenyl, $C_6$–$C_{20}$ aryl, $C_7$–$C_{40}$ alkylaryl, $C_8$–$C_{20}$ arylalkenyl, alkoxy siloxy, and combinations thereof;

A groups are equal to or different from each other, wherein A is a bridge group between L and Q, wherein a is selected from the group consisting of one divalent atom of group 16, a trivalent monosubstituted element of group 15, a tetravalent disubstituted element of group 14, and a chain of 2 or more atoms substituted or not substituted;

o is a number of value 0 or 1;

k is a number of value 1, 2, or 3;

m is a number equal to or higher than 2 and coinciding with an oxidation state of the transition metal;

p, n, 1 are numbers of value 0 or 1;

j is a number of value 0 or 1; when j is equal to 1 and o is equal to 0, Q is a silicon, germanium, or tin atom; with a proviso that the compound does not have a general formula of;

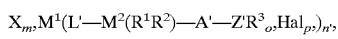

wherein $M^1$ is a metal of group 4, 5 or 6 of the periodic table, each X is independently selected from the group consisting of hydrogen, halogen, and a $C_1$–$C_{40}$ carbon-containing rest; m' is equal to 1, 2 or 3; n' is equal to 1 or 2; each L' is independently a $\pi$ ligand, wherein L' coordinates to $M^1$; each $M^2$ is independently selected from the group consisting of silicon, germanium, and tin; $R^1$ is a $C_1$–$C_{20}$ carbon-containing group; $R^2$ is a $C_1$–$C_{20}$ carbon-containing group or a $\pi$ ligand, wherein $R^2$ coordinates to $M^1$; each A' is independently a divalent $C_1$–$C_{40}$ carbon-containing rest; each z' is independently selected from the group consisting of boron, silicon, germanium, and tin; each $R^3$ is independently selected from the group consisting of hydrogen and a $C_1$–$C_{20}$ carbon-containing rest; o' is equal to 0, 1, or 2; each Hal is independently selected from the group consisting of halogen atoms; and p' is equal to 1, 2, or 3.

3. A process for synthesizing metallocene compound as claimed in claim 1, wherein the process is set forth below:

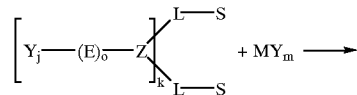

wherein:

Y, Z, L, E, M, j, m, and o are defined in claim 1; and S is a leaving group united to the cyclopentadienyl group.

4. A process according to claim 3 wherein each S represents is independently selected from the group consisting of $Si(CH_3)_3$ and $Sn(CH_3)_3$.

5. A process according to claim 3 wherein L—S represents an ionic, s, or p bond or combinations thereof; and L—M represents a bond with a high type $\pi$ character.

6. A process for synthesizing a metallocene derivative, the process comprising reacting a functionalized bridge of the compound of claim 1 with a substrate that has one or more reactive groups represented by G—J, wherein G is an element of group 14, 15, 16, or 17, and wherein J is an element of group 1 or 2.

7. A process according to claim 6 wherein G—J is selected from the group consisting of hydroxyl, amino, phosphino, and thiol.

8. A process according to claim 6 wherein the substrate is a polyol.

9. A process according to claim 6 wherein the substrate is a diol.

10. A metallocene compound according to claim 2, wherein A is selected from the group consisting of: —O—, >N—R, >C(R)$_2$, >Si(R)$_2$, —C—C—, —C—Si—, —Si—Si—, —Si—O—, —C—O—, —C—O, —C—N—, —C—C—C—, —C—Si—C—, and —Si—O—Si—.

11. A process as claimed in claim 3, wherein S is $T(R^4)_3$, wherein T is silicon, germanium, or tin, and wherein $R^4$ is $C_1$–$C_{20}$ alkyl.

12. A process for synthesizing a metallocene derivative, the process comprising reacting a functionalized bridge of the compound of claim 1 with a substrate that has a reactive group, wherein the reactive group comprises an element of group 14, 15, 16, or 17 and further comprises an element of group 1 or 2.

13. A process according to claim 12 wherein the reactive group is selected from the group consisting of hydroxyl, amino, phosphino, and thiol.

14. A process according to claim 12 wherein the reactive group is selected from the group consisting of hydroxyl, amino, phosphino, thiol, amido, phosphido, and thioxy.

15. A process according to claim 12 wherein the substrate is a polyol.

16. A process according to claim 12 wherein the substrate is a diol.

17. A metallocene compound selected from the group consisting of:

methyl-chloro-silanediyl-bis(cyclopentadienyl) zirconiumdichloride;

methyl-chloro-silanediyl(cyclopentadienyl) (tetramethylcyclopentadienyl) zirconiumdichloride;

methyl-chloro-silanediyl(cyclopentadienyl)1-indenyl) zirconiumdichloride;

methyl-chloro-silanediyl(cyclopentadienyl)(1-(2-methy)indenyl) zirconiumdichloride;
methyl-chloro-silanediyl(cyclopentadienyl)(9-fluorenyl) zirconiumdichloride;
methyl-chloro-silanediyl bis(tetramethylcyclopentadienyl) zirconiumdichloride;
methyl-chloro-silanediyl(tetramethylcyclopentadienyl)(1-(2-methy)indenyl) zirconiumdichloride;
methyl-chloro-silanediyl(tetramethylcyclopentadienyl)(1-indenyl) zirconiumdichloride;
methyl-chloro-silanediyl(tetramethylcyclopentadienyl)(9-fluorenyl) zirconiumdichloride;
methyl-chloro-silanediyl bis (1-(2-methy)indenyl) zirconiumdichloride;
methyl-chloro-silanediyl(1-(2-methy)indenyl)(1-indenyl) zirconiumdichloride;
methyl-chloro-silanediyl(1-(2-methy)indenyl)(9-fluorenyl) zirconiumdichloride;
methyl-chloro-silanediyl bis(1-indenyl) zirconiumdichloride;
methyl-chloro-silanediyl(9-fluorenyl)(1-indenyl) zirconiumdichloride;
methyl-chloro-silanediyl bis(9-fluorenyl) zirconiumdichloride;
methyl-chloro-silanediyl bis(cyclopentadienyl) hafniumdichloride;
methyl-chloro-silanediyl(cyclopentadiunyl) tetramethylcyclopentadienyl) hafniumdichloride;
methyl-chloro-silanediyl(cyclopentadienyl)(1-indenyl) hafniumdichloride;
methyl-chloro-silanediyl(cyclopentadienyl)(1-(2-methy)indenyl) hafniumdichloride;
methyl-chloro-silanediyl(cyclopentadienyl)(9-fluorenyl) hafniumdichloride;
methyl-chloro-silanediyl bis(tetramethylcyclopentadienyl) hafniumdichloride;
methyl-chloro-silanediyl bis(tetramethylcyclopentadienyl)(1-(2-methy)indenyl) hafniumdichloride;
methyl-chloro-silanediyl(tetramethylcyclopentadienyl)(1-indenyl) hafniumdichloride;
methyl-chloro-silanediyl(tetramethylcyclopentadienyl)(9-fluorenyl) hafniumdichloride;
methyl-chloro-silanediyl bis (1-(2-methy)indenyl) hafniumdichloride;
methyl-chloro-silanediyl(1-(2-methy)indenyl)(1-indenyl) hafniumdichloride;
methyl-chloro-silanediyl(1-(2-methy)indenyl)(9-fluorenyl) hafniumdichloride;
methyl-chloro-silanediyl bis(1-indenyl) hafniumdichloride;
methyl-chloro-silanediyl(9-fluorenyl)(1-indenyl) hafniumdichloride;
methyl-chloro-silanediyl(9-fluorenyl) hafniumdichloride;
methyl-chloro-silanediyl-bis(cyclopentadienyl) titaniumdichloride;
methyl-chloro-silanediyl(cyclopentadienyl) (tetramethylcyclopentadienyl) titaniumdichloride;
methyl-chloro-silanediyl(cyclopentadienyl)(1-indenyl) titaniumdichloride;
methyl-chloro-silanediyl(cyclopentadienyl)(1-(2-methy)indenyl) titaniumdichloride;
methyl-chloro-silanediyl(cyclopentadienyl)(9-fluorenyl) titaniumdichloride;
methyl-chloro-silanediyl bis(cyclopentadienyl) titaniumdichloride;
methyl-chloro-silanediyl(tetramethylcyclopentadienyl)(1-(2-methy)indenyl) titaniumdichloride;
methyl-chloro-silanediyl(tetramethylcyclopentadienyl)(1-indenyl) titaniumdichloride;
methyl-chloro-silanediyl(tetramethylcyclopentadienyl)(9-fluorenyl) titaniumdichloride;
methyl-chloro-silanediyl bis (1-(2-methy)indenyl) titaniumdichloride;
methyl-chloro-silanediyl(1-(2-methy)indenyl)(1-indenyl) titaniumdichloride;
methyl-chloro-silanediyl(1-(2-methy)indenyl)(9-fluorenyl) titaniumdichloride;
methyl-chloro-silanediyl bis(1-indenyl) titaniumdichloride;
methyl-chloro-silanediyl(9-fluorenyl)(1-indenyl) titaniumdichloride;
methyl-chloro-silanediyl bis(9-fluorenyl) titaniumdichloride;
ethyl-chloro-silanediyl bis(cyclopentadienyl) zirconiumdichloride;
ethyl-chloro-silanediyl(cyclopentadiunyl) (tetramethylcyclopentadienyl) zirconiumdichloride;
ethyl-chloro-silanediyl(cyclopentadienyl)(1-indenyl) zirconiumdichloride;
ethyl-chloro-silanediyl(cyclopentadienyl)(1-(2-methy)indenyl) zirconiumdichloride;
ethyl-chloro-silanediyl(cyclopentadienyl)(9-fluorenyl) zirconiumdichloride;
ethyl-chloro-silanediyl bis(tetramethylcyclopentadienyl) zirconiumdichloride;
ethyl-chloro-silanediyl(tetramethylcyclopentadienyl)(1-(2-methy)indenyl) zirconiumdichloride;
ethyl-chloro-silanediyl(tetramethylcyclopentadienyl)(1-indenyl) zirconiumdichloride;
ethyl-chloro-silanediyl(tetramethylcyclopentadienyl)(9-fluorenyl) zirconiumdichloride;
ethyl-chloro-silanediyl bis (1-(2-methy)indenyl) zirconiumdichloride;
ethyl-chloro-silanediyl(1-(2-methy)indenyl)(1-indenyl) zirconiumdichloride;
ethyl-chloro-silanediyl(1-(2-methy)indenyl)(9-fluorenyl) zirconiumdichloride;
ethyl-chloro-silanediyl bis(1-indenyl) zirconiumdichloride;
ethyl-chloro-silanediyl(9-fluorenyl)(1-indenyl) zirconiumdichloride;
ethyl-chloro-silanediyl bis(9-fluorenyl) zirconiumdichloride;
ethyl-chloro-silanediyl-bis(cyclopentadienyl) hafniumdichloride;
ethyl-chloro-silanediyl(cyclopentadienyl) (tetramethylcyclopentadienyl) hafniumdichloride;
ethyl-chloro-silanediyl(cyclopentadienyl)(1-indenyl) hafniumdichloride;
ethyl-chloro-silanediyl(cyclopentadienyl)(1-(2-methy)indenyl) hafniumdichloride
ethyl-chloro-silanediyl(cyclopentadienyl)(9-fluorenyl) hafniumdichloride;
ethyl-chloro-silanediyl bis(tetramethylcyclopentadienyl) hafniumdichloride;
ethyl-chloro-silanediyl(tetramethylcyclopentadienyl)(1-(2-methy)indenyl) hafniumdichloride;
ethyl-chloro-silanediyl(tetramethylcyclopentadienyl)(1-indenyl) hafniumdichloride;
ethyl-chloro-silanediyl(tetramethylcyclopentadienyl)(9-fluorenyl) hafniumdichloride;
ethyl-chloro-silanediyl bis (1-(2-methy)indenyl) hafniumdichloride;
ethyl-chloro-silanediyl(1-(2-methy)indenyl)(1-indenyl) hafniumdichloride;
ethyl-chloro-silanediyl(1-(2-methy)indenyl)(9-fluorenyl) hafniumdichloride;
ethyl-chloro-silanediyl bis(1-indenyl) hafniumdichloride;

ethyl-chloro-silanediyl(9-fluorenyl)(1-indenyl) hafniumdichloride;
ethyl-chloro-silanediyl bis(9-fluorenyl) hafniumdichloride;
ethyl-chloro-silanediyl bis(cyclopentadienyl) titaniumdichloride;
ethyl-chloro-silanediyl(cyclopentadiunyl) tetramethylcyclopentadienyl) titaniumdichloride;
ethyl-chloro-silanediyl(cyclopentadienyl)(1-indenyl) titaniumdichloride;
ethyl-chloro-silanediyl(cyclopentadienyl)(1-(2-methy)indenyl) titaniumdichloride;
ethyl-chloro-silanediyl(cyclopentadienyl)(9-fluorenyl) titaniumdichloride;
ethyl-chloro-silanediyl bis(tetramethylcyclopentadienyl) titaniumdichloride;
ethyl-chloro-silanediyl(tetramethylcyclopentadienyl)(1-(2-methy)indenyl) titaniumdichloride;
ethyl-chloro-silanediyl(tetramethylcyclopentadienyl)(1-indenyl) titaniumdichloride;
ethyl-chloro-silanediyl(tetramethylcyclopentadienyl)(9-fluorenyl) titaniumdichloride;
ethyl-chloro-silanediyl bis (1-(2-methy)indenyl) titaniumdichloride;
ethyl-chloro-silanediyl(1-(2-methy)indenyl)(1-indenyl) titaniumdichloride;
ethyl-chloro-silanediyl(1-(2-methy)indenyl)(9-fluorenyl) titaniumdichloride;
ethyl-chloro-silanediyl bis(1-indenyl) titaniumdichloride;
ethyl-chloro-silanediyl(9-fluorenyl)(1-indenyl) titaniumdichloride;
ethyl-chloro-silanediyl bis(9-fluorenyl) titaniumdichloride;
propyl-chloro-silanediyl-bis(cyclopentadienyl) zirconiumdichloride;
propyl-chloro-silanediyl(cyclopentadienyl) (tetramethylcyclopentadienyl) zirconiumdichloride;
propyl-chloro-silanediyl(cyclopentadienyl)(1-indenyl) zirconiumdichloride;
propyl-chloro-silanediyl(cyclopentadienyl)(1-(2-methy)indenyl) zirconiumdichloride;
propyl-chloro-silanediyl(cyclopentadienyl)(9-fluorenyl) zirconiumdichloride;
propyl-chloro-silanediyl bis(cyclopentadienyl) zirconiumdichloride;
propyl-chloro-silanediyl(tetramethylcyclopentadienyl)(1-(2-methy)indenyl) zirconiumdichloride;
propyl-chloro-silanediyl(tetramethylcyclopentadienyl)(1-indenyl) zirconiumdichloride;
propyl-chloro-silanediyl(tetramethylcyclopentadienyl)(9-fluorenyl) zirconiumdichloride;
propyl-chloro-silanediyl bis (1-(2-methy)indenyl) zirconiumdichloride;
propyl-chloro-silanediyl(1-(2-methy)indenyl)(1-indenyl) zirconiumdichloride;
propyl-chloro-silanediyl(1-(2-methy)indenyl)(9-fluorenyl) zirconiumdichloride;
propyl-chloro-silanediyl bis(1-indenyl) zirconiumdichloride;
propyl-chloro-silanediyl(9-fluorenyl)(1-indenyl) zirconiumdichloride;
propyl-chloro-silanediyl bis(9-fluorenyl) zirconiumdichloride;
propyl-chloro-silanediyl-bis(cyclopentadienyl) hafniumdichloride;
propyl-chloro-silanediyl(cyclopentadiunyl) (tetramethylcyclopentadienyl) hafniumdichloride;
propyl-chloro-silanediyl(cyclopentadienyl)(1-indenyl) hafniumdichloride;
propyl-chloro-silanediyl(cyclopentadienyl)(1-(2-methy)indenyl) hafniumdichloride;
propyl-chloro-silanediyl(cyclopentadienyl)(9-fluorenyl) hafniumdichloride;
propyl-chloro-silanediyl bis(tetramethylcyclopentadienyl) hafniumdichloride;
propyl-chloro-silanediyl(tetramethylcyclopentadienyl)(1-(2-methy)indenyl) hafniumdichloride;
propyl-chloro-silanediyl(tetramethylcyclopentadienyl)(1-indenyl) hafniumdichloride;
propyl-chloro-silanediyl(tetramethylcyclopentadienyl)(9-fluorenyl) hafniumdichloride;
propyl-chloro-silanediyl bis (1-(2-methy)indenyl) hafniumdichloride;
propyl-chloro-silanediyl(1-(2-methy)indenyl)(1-indenyl) hafniumdichloride;
propyl-chloro-silanediyl(1-(2-methy)indenyl)(9-fluorenyl) hafniumdichloride;
propyl-chloro-silanediyl bis(1-indenyl) hafniumdichloride;
propyl-chloro-silanediyl(9-fluorenyl)(1-indenyl) hafniumdichloride ;
propyl-chloro-silanediyl bis(9-fluorenyl) hafniumdichloride ;
propyl-chloro-silanediyl-bis(cyclopentadienyl) titaniumdichloride;
propyl-chloro-silanediyl(cyclopentadienyl) (tetramethylcyclopentadienyl) titaniumdichloride;
propyl-chloro-silanediyl(cyclopentadienyl)(1-indenyl) titaniumdichloride;
propyl-chloro-silanediyl(cyclopentadienyl)(1-(2-methy)indenyl) titaniumdichloride;
propyl-chloro-silanediyl(cyclopentadienyl)(9-fluorenyl) titaniumdichloride;
propyl-chloro-silanediyl bis(cyclopentadienyl) titaniumdichloride;
propyl-chloro-silanediyl(tetramethylcyclopentadienyl)(1-(2-methy)indenyl) titaniumdichloride;
propyl-chloro-silanediyl(tetramethylcyclopentadienyl)(1-indenyl) titaniumdichloride;
propyl-chloro-silanediyl(tetramethylcyclopentadienyl)(9-fluorenyl) titaniumdichloride;
propyl-chloro-silanediyl bis(1-(2-methy)indenyl) titaniumdichloride;
propyl-chloro-silanediyl(1-(2-methy)indenyl)(1-indenyl) titaniumdichloride;
propyl-chloro-silanediyl(1-(2-methy)indenyl)(9-fluorenyl) titaniumdichloride;
propyl-chloro-silanediyl bis(1-indenyl) titaniumdichloride;
propyl-chloro-silanediyl(9-fluorenyl)(1-indenyl) titaniumdichloride; and
propyl-chloro-silanediyl bis(9-fluorenyl) titaniumdichloride.

18. A metallocene compound selected from the group consisting of:
((chloromethylsilanodiyl)bis(cyclopentadienyl)) zirconium(IV)dichloride; and
((chloromethylsilanodiyl)bis(cyclopentadienyl))hafnium (IV)dichloride.

19. A metallocene derivative selected from the group consisting of: $Cl_2HfCp_2Si(CH_3)$—O—$(CH_3)SiCp_2HfCl_2$; $PhCH_2O(CH_3)SiCp_2ZrCl_2$; $Cl_2ZrCp_2Si(CH_3)$—$OCH_2C_6H_4CH_2O$—$(CH_3)SiCp_2ZrCl_2$; $HOCH_2C_6H_4CH_2O$—$(CH_3)SiCp_2ZrCl_2$; and $Cl_2ZrCp_2Si(CH_3)$—O—$(CH_3)SiCp_2ZrCl_2$;

wherein each $C_p$ is independently selected from the group consisting of a cyclopentadienyl ring, a substituted cyclopentadienyl ring, a substituted indenyl ring, a nonsubstituted indenyl ring, a substituted fluorenyl ring, and a nonsubstituted indenyl ring.
20. A metallocene compound selected from the group consisting of:
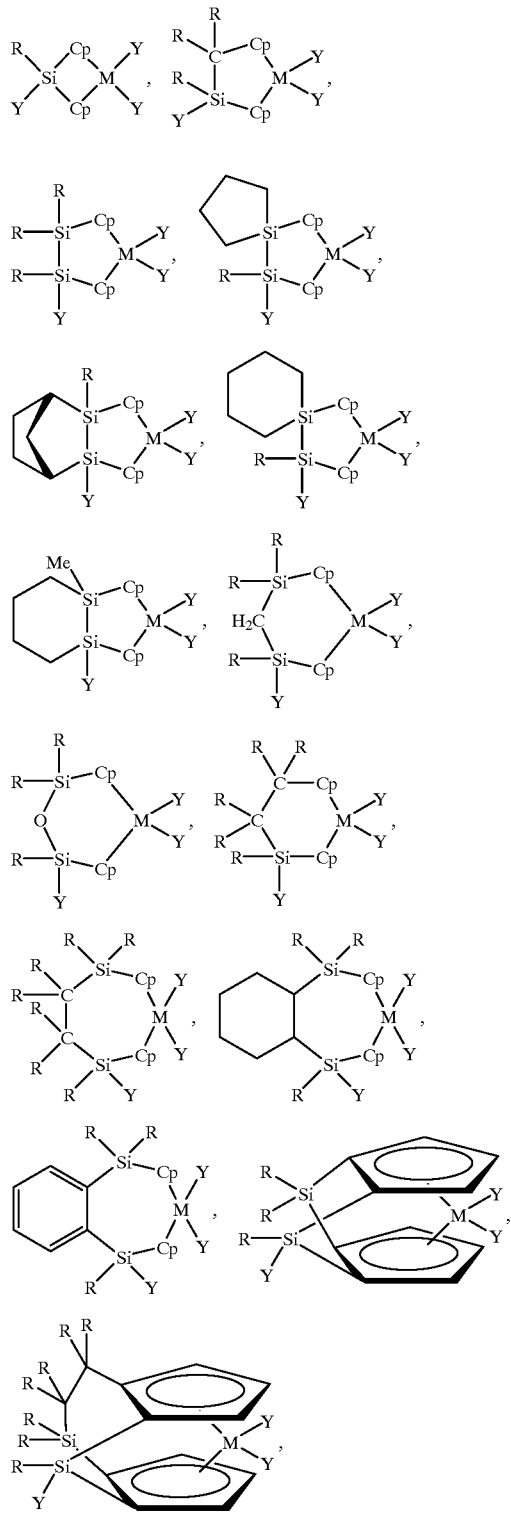
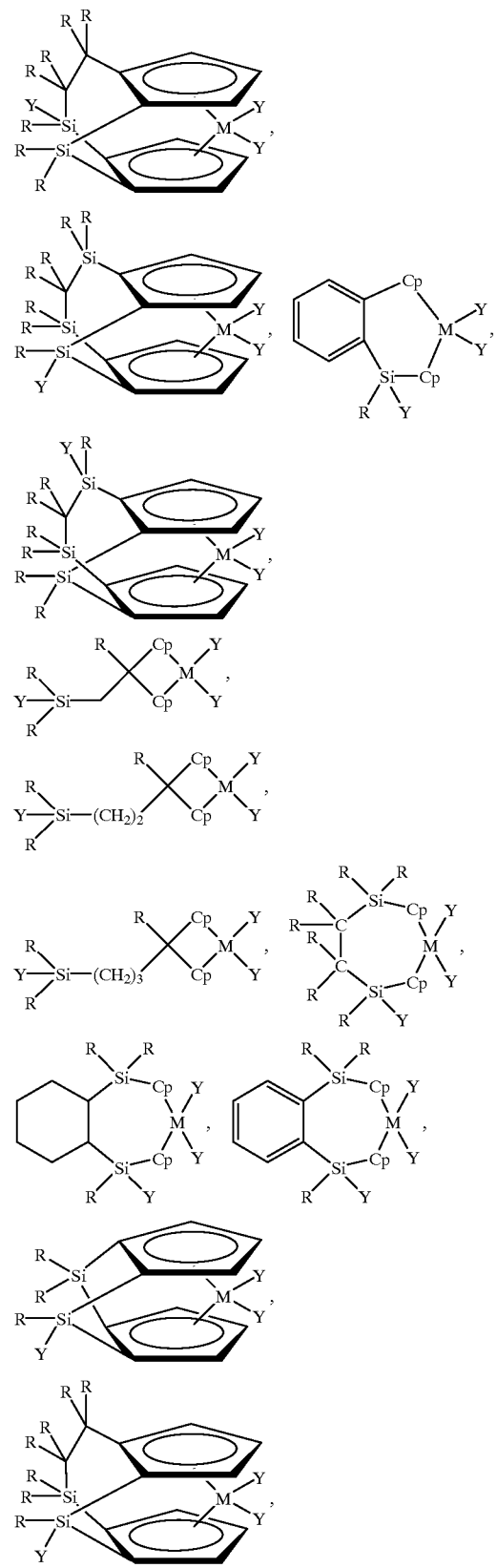

-continued

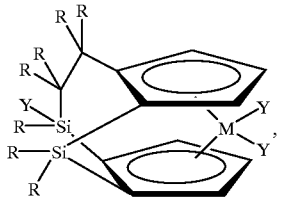

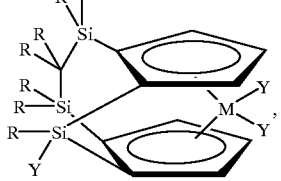
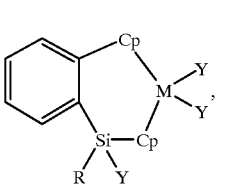

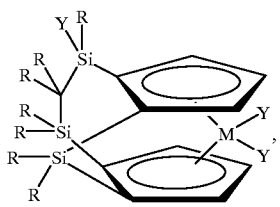

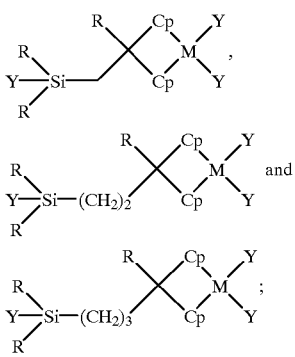

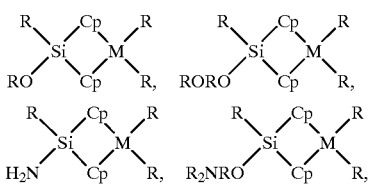

wherein Y is halogen;

wherein M is a transition metal of group 3, 4, 5 or 6 of the periodic table;

wherein R is selected from the group consisting of hydrogen, halogen, halocarbon, substituted halocarbon, $C_1$–$C_{20}$ alkyl, $C_2$–$C_{20}$ alkenyl, $C_6$–$C_{20}$ aryl, $C_7$–$C_{40}$ alkylaryl, $C_8$–$C_{20}$ arylalkenyl, alkoxy, siloxy, and combinations thereof; and wherein each $C_p$ is independently selected from the group consisting of a cyclopentadienyl ring, a substituted cyclopentadienyl ring, a substituted indenyl ring, a nonsubstituted indenyl ring, a substituted fluorenyl ring, and a nonsubstituted indenyl ring.

21. A metallocene derivative selected from the group consisting of:

-continued

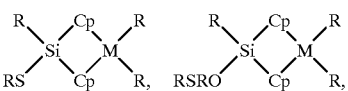

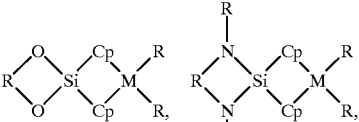

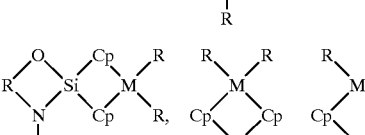

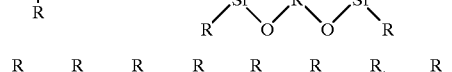

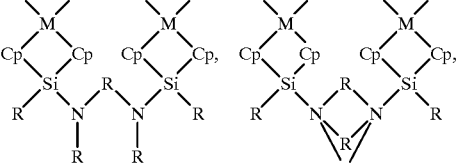

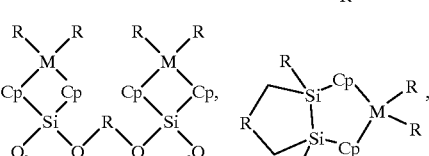

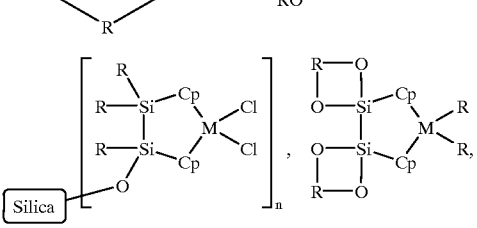

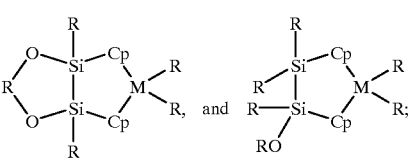

wherein M is a transition metal of group 3, 4, 5 or 6 of the periodic table;

wherein R is selected from the group consisting of hydrogen, halogen, halocarbon, substituted halocarbon, $C_1$–$C_{20}$ alkyl, $C_2$–$C_{20}$ alkenyl, $C_6$–$C_{20}$ aryl, $C_7$–$C_{40}$ alkylaryl, $C_8$–$C_{20}$ arylalkenyl, alkoxy, siloxy, and combinations thereof; and wherein each $C_p$ is independently selected from the group consisting of a cyclopentadienyl ring, a substituted cyclopentadienyl ring, a substituted indenyl ring, a nonsubstituted indenyl ring, a substituted fluorenyl ring, and a nonsubstituted indenyl ring.

* * * * *

UNITED STATES PATENT AND TRADEMARK OFFICE
CERTIFICATE OF CORRECTION

PATENT NO.    : 6,018,064
DATED         : January 25, 2000
INVENTOR(S)   : Mendez Llatas et al.

It is certified that error appears in the above-identified patent and that said Letters Patent is hereby corrected as shown below:

Column 16,
Line 28, delete "spacer"; and change "that unites Z and Y and can have" to -- hanving --.
Line 33, change "Y" to -- $Y_j$ --.
Line 43, after "Z"; insert -- wherein each 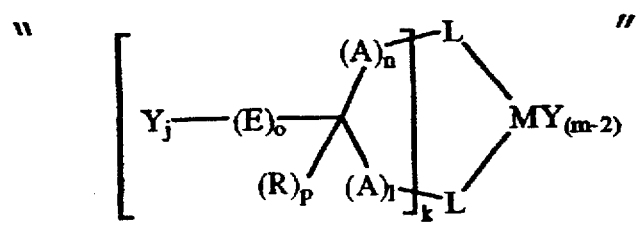 group is the same or different and wherein j is equal to 1 in at least one 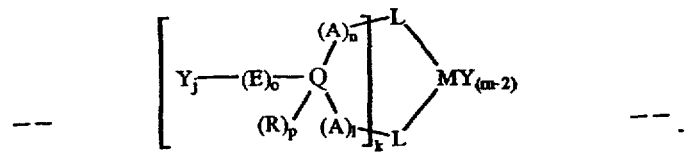 group; --

Column 17,
Line 5, change

"
$$\left[ Y_j \!-\!\!(E)_o \!\!\begin{array}{c} (A)_n \!\!-\!\! L \\ \diagup \quad \diagdown \\ \diagdown \quad \diagup \\ (R)_p \; (A)_h \!\!-\!\! L \end{array}\!\! MY_{(m-2)} \right]$$
"

to $$\left[ Y_j \!-\!\!(E)_o \!\!-\! Q \!\!\begin{array}{c} (A)_n \!\!-\!\! L \\ \diagup \quad \diagdown \\ \diagdown \quad \diagup \\ (R)_p \; (A)_h \!\!-\!\! L \end{array}\!\! MY_{(m-2)} \right]$$

-- .

UNITED STATES PATENT AND TRADEMARK OFFICE
CERTIFICATE OF CORRECTION

PATENT NO. : 6,018,064
DATED : January 25, 2000
INVENTOR(S) : Mendez Llatas et al.

It is certified that error appears in the above-identified patent and that said Letters Patent is hereby corrected as shown below:

Column 17,
Line 22, delete "spacer"; and change "that unites Q and Y and can have" to -- having --.
Line 28, change "Y" to -- $Y_j$ --.
Line 48, after "atom;" insert
-- wherein each 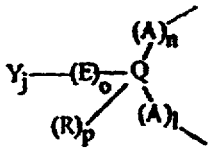 group is the same or different and wherein j is equal to 1 in at least one group; -- 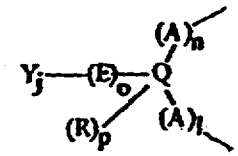

Column 18,
Line 3, change "compound" to -- compounds --.
Line 10, change

" " 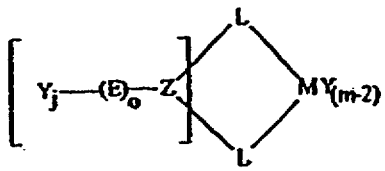

UNITED STATES PATENT AND TRADEMARK OFFICE
CERTIFICATE OF CORRECTION

PATENT NO. : 6,018,064
DATED : January 25, 2000
INVENTOR(S) : Mendez Llatas et al.

It is certified that error appears in the above-identified patent and that said Letters Patent is hereby corrected as shown below:

to

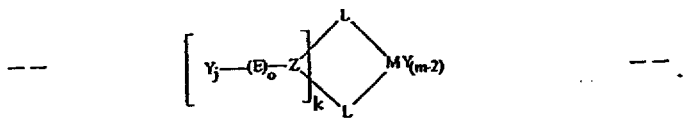

Column 23,
Line 2, change "indenyl" to -- fluorenyl --.

Column 25,
Line 55, change "indenyl" to -- fluorenyl --.

Column 26,
Line 63, change "indenyl" to -- fluorenyl --.

Signed and Sealed this

Thirteenth Day of November, 2001

Attest:

NICHOLAS P. GODICI
Attesting Officer   Acting Director of the United States Patent and Trademark Office